US008556626B2

(12) United States Patent
Evenson

(10) Patent No.: US 8,556,626 B2
(45) Date of Patent: *Oct. 15, 2013

(54) MANDIBLE POSITION INDICATOR FOR MEASURING AND REPLICATING OCCLUSION

(71) Applicant: NorthPointe Holding Company LLC, Minnetonka, MN (US)

(72) Inventor: Roger A. Evenson, Saint Paul, MN (US)

(73) Assignee: NorthPointe Holding Company LLC, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,269

(22) Filed: Nov. 7, 2012

(65) Prior Publication Data

US 2013/0130195 A1 May 23, 2013

Related U.S. Application Data

(63) Continuation-in-part of application No. 12/714,164, filed on Feb. 26, 2010, now Pat. No. 8,348,667.

(60) Provisional application No. 61/156,373, filed on Feb. 27, 2009, provisional application No. 61/619,667, filed on Apr. 3, 2012.

(51) Int. Cl.
*A61C 7/00* (2006.01)
(52) U.S. Cl.
USPC .............................................. 433/68; 433/54
(58) Field of Classification Search
USPC .............................. 433/54, 56, 57, 68, 69, 73
See application file for complete search history.

(56) References Cited

U.S. PATENT DOCUMENTS

| 2,814,876 | A | | 12/1957 | Stuart |
| 3,724,099 | A | | 4/1973 | Stuart |
| 3,818,595 | A | | 6/1974 | Stuart |
| 3,896,551 | A | | 7/1975 | Stuart |
| 4,014,097 | A | * | 3/1977 | Pameijer ......................... 433/27 |
| 4,204,326 | A | * | 5/1980 | Dimeff ............................ 433/50 |

(Continued)

FOREIGN PATENT DOCUMENTS

WO   WO-2008/080235 A1   7/2008

OTHER PUBLICATIONS

"U.S. Appl. No. 12/714,164, Response filed Aug. 20, 2012 to Ex Parte Quayle Action mailed Jun. 20, 2012", 9 pgs.

(Continued)

*Primary Examiner* — Ralph Lewis
(74) *Attorney, Agent, or Firm* — Schwegman Lundberg & Woessner, P.A.

(57) ABSTRACT

One embodiments of the present subject matter include a method that includes fixing a top pantograph to a patient via clutches to the top teeth of the patient, fixing a bottom pantograph to a patient via clutches to the bottom teeth of the patient, optically monitoring the bite of the patient by monitoring the relation of the top pantograph to the bottom pantograph during a bite cycle, storing data relating to the actual bite storing patient data including a three-dimensional model including a top teeth model and a bottom teeth model, storing a digital top pantograph model associated with the top pantograph, storing a digital bottom pantograph model associated with the bottom pantograph, digitally pairing the bite data, the top pantograph model and the bottom pantograph model to the patient data, and digitally modeling the bite.

20 Claims, 14 Drawing Sheets

(56) References Cited

U.S. PATENT DOCUMENTS

| | | | |
|---|---|---|---|
| 4,354,836 A | 10/1982 | Santoni | |
| 4,468,198 A | 8/1984 | Kataoka et al. | |
| 4,482,320 A * | 11/1984 | Kataoka et al. | 433/69 |
| 4,501,556 A | 2/1985 | Zelnigher | |
| 4,639,220 A | 1/1987 | Nara et al. | |
| 4,681,539 A | 7/1987 | Knap | |
| 4,859,181 A | 8/1989 | Neumeyer | |
| 5,006,065 A * | 4/1991 | Waysenson | 433/63 |
| 5,026,282 A | 6/1991 | Koike | |
| 5,143,086 A | 9/1992 | Duret et al. | |
| 5,320,528 A | 6/1994 | Alpern et al. | |
| 5,340,309 A * | 8/1994 | Robertson | 433/69 |
| 5,738,517 A | 4/1998 | Keller | |
| 6,120,290 A * | 9/2000 | Fukushima et al. | 433/69 |
| 6,152,731 A * | 11/2000 | Jordan et al. | 433/69 |
| 6,152,732 A | 11/2000 | Lindekugel | |
| 6,322,359 B1 | 11/2001 | Jordan | |
| 6,558,161 B2 | 5/2003 | Nagata | |
| 6,726,479 B2 | 4/2004 | Tremont | |
| 7,048,539 B2 | 5/2006 | Mack | |
| 7,182,737 B2 * | 2/2007 | Kim et al. | 600/590 |
| 7,347,690 B2 | 3/2008 | Jordan | |
| 7,433,810 B2 | 10/2008 | Pavloskaia et al. | |
| 8,021,149 B2 * | 9/2011 | Gutman et al. | 433/69 |
| 8,348,667 B2 * | 1/2013 | Evenson | 433/68 |
| 2002/0048741 A1 | 4/2002 | Jordan et al. | |
| 2008/0057466 A1 | 3/2008 | Jordan et al. | |
| 2008/0261168 A1 * | 10/2008 | Gutman et al. | 433/69 |
| 2008/0261169 A1 | 10/2008 | Gutman et al. | |
| 2009/0068618 A1 * | 3/2009 | Lang | 433/214 |
| 2011/0027745 A1 | 2/2011 | Evenson | |
| 2011/0217674 A1 * | 9/2011 | Hanewinkel et al. | 433/140 |

OTHER PUBLICATIONS

"U.S. Appl. No. 12/714,164, Ex Parte Quayle Action mailed Jun. 20, 2012", 5 pgs.

"U.S. Appl. No. 12/714,164, Notice of Allowance, mailed Sep. 7, 2012", 5 pgs.

"U.S. Appl. No. 12/714,164, PTO Response to 312 Amendment mailed Dec. 6, 2012", 2 pgs.

"CONDYLOCOMP® LR3 Brochure", DENTRON GmbH, (Prior to Feb. 26, 2009), 4 pgs.

* cited by examiner

MANDIBLE POSITION INDICATOR FOR MEASURING AND REPLICATING OCCLUSION

CROSS-REFERENCE TO RELATED APPLICATIONS

This application is a continuation-in-part of U.S. patent application Ser. No. 12/714,164, entitled "Mandible Position Indicator and Automatic Articulator for Measuring and Replicating Occlusion," filed Feb. 26, 2012, which claims the benefit of U.S. Provisional Application No. 61/156,373, filed Feb. 27, 2009, the disclosure of each of which is incorporated herein by reference in its entirety.

This application claims the benefit of U.S. Provisional Application No. 61/619,667, filed Apr. 3, 2012, the disclosure of which is incorporated herein by reference in its entirety.

BACKGROUND

Dental care providers may create a three dimensional ("3D") physical model or cast of one or more areas of a patient's oral cavity. With a 3D physical model, a care provider can interact with the model to quickly view multiple angles of the model and to visualize adjustments made to the model. For example, care providers may create a model of an area of a patient's oral cavity where one or more teeth are missing or damaged, so that suitable replacement teeth may be made in the lab using the model as a guide.

Proper fitting the lab-made teeth would benefit from an understanding of how the teeth are used by the patient. In other words, somehow linking the model to the mechanics of the patient's bite is desirable. In the past, care providers have used a mechanical device called an articulator in conjunction with the models to replicate movement of the patient's mandible about a bite axis. This is a crude replication of the bite and often fails to capture intricacies of the bite motion, including habitual adaptation of the bite to malformations of the teeth. Habitual adaptation of the bite often occurs via muscle training In addition to failing to capture the complex curvature of the bite, the known methods are imprecise and inaccurate, as the care provider is often mounted to soft tissue, record data via a pen, or introduce error during different portions of a procedure. Articulators are manually adjusted based on recorded data. This provides two windows for errors. A third window for error is in model creation. What is needed is a system which can accurately and precisely capture bite motion and simulate bite motion so that a care provide can better study bite motion. To reach a better understanding of a patient's physiology and proposed care options, care providers have expressed a desire to be able to study bite motion physically, rather than in 2 dimensions.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The present subject matter provides an improved system and method for capturing dental articulation. It allows care providers to understand articulation, create models of that articulation, find improved articulation if possible, and provide treatments based on the models that will either allow the existing articulation or encourage the improved articulation.

The following benefits are recognized. First, the present subject matter better captures bite motion by fixing measuring tools to both the top and bottom teeth. This is preferred over systems that fix to only one row of teeth, as it reduces error. Systems that fix to only one row of teeth inevitably fix the other portion of a bite monitoring system to soft tissue, which can result in error via tissue movement or some other error. This problem is discussed herein. Improvements over this approach by the present subject matter include actually replicating the function of the condylar axis, as well as eliminating the reliance on soft tissue or some other error prone data in establishing the geometric relationship of both rows of teeth to one another throughout a range of mandibular articulations.

Second, the present subject matter better simulates motion by using digital data to replicate a bite motion on an improved automated articulator, which can include a Stewart platform.

By recording bite motion in a digital format, and then simulating the bite motion using the digital motion, at least one opportunity for error is eliminated. One opportunity for error is eliminated because data from the monitor is transcribed to the articulator digitally, rather than being replicated by hand adjustments to the articulator.

Figure 1:
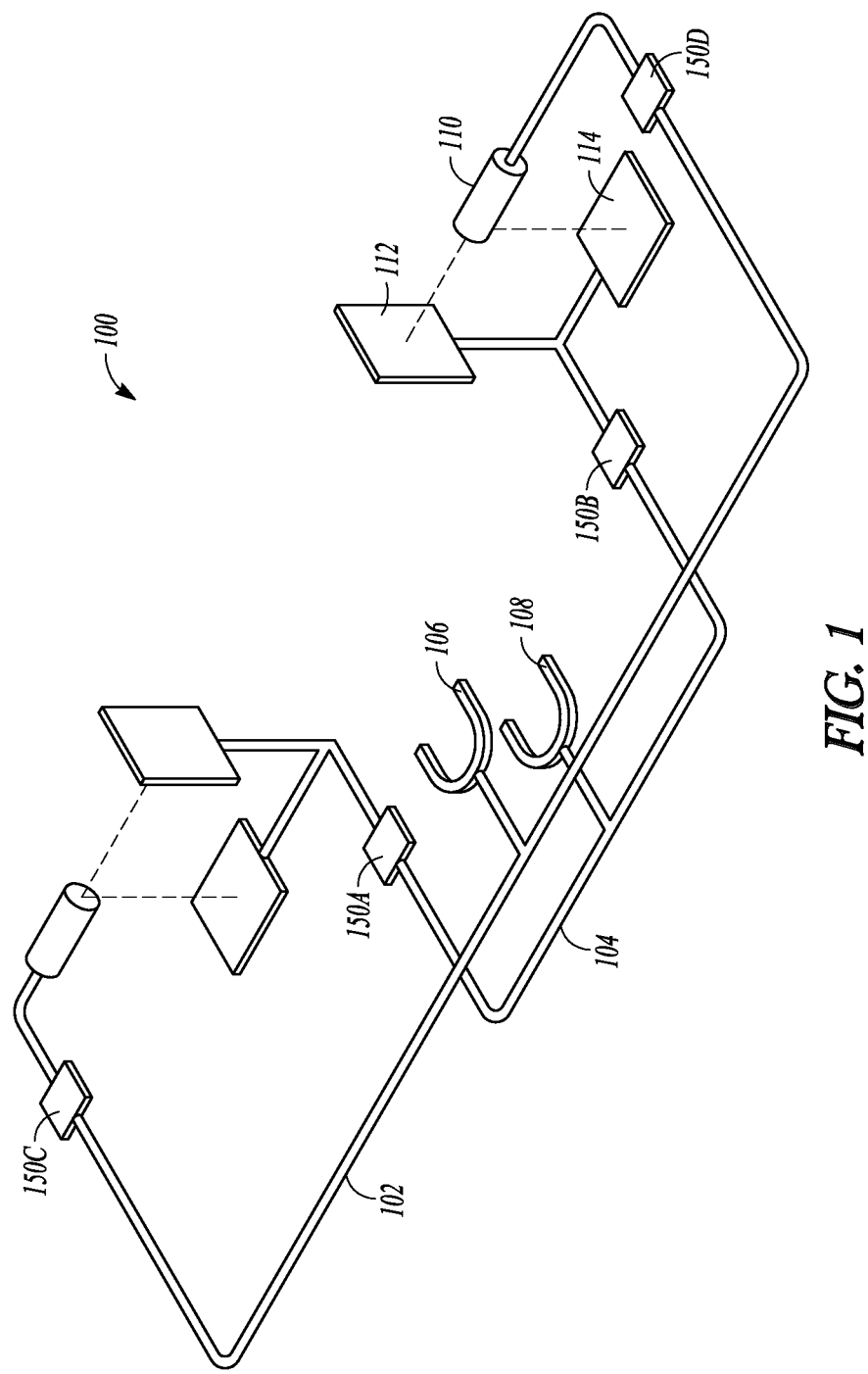
FIG. 1 is an illustration of a digital bite information collection apparatus 100, according to some embodiments.

FIG. 1 is an illustration of a digital bite information collection apparatus 100, according to some embodiments. The system includes a top face bow 102 coupled to a top clutch 106. The top clutch can be coupled to a top teeth and optionally gingivia of a patient, such as by using a quick setting, compliant compound that can both capture the shape of the teeth and which can be released from the teeth. The system 100 further includes a bottom face bow 104 coupled to a bottom teeth 108, which can have a compound disposed in it just as the top face bow 102 does.

When mounted, the care provided can adjust the face bows 102, 104 so that a first sensor 110 registers with both an anterior-posterior sensor field 112 and a horizontal sensor field 114. This adjustment can optionally be performed using adjustable sliders 150A-D. This allows the tool to fit to persons in different stages of development.

The first sensor 110 is a laser in some embodiments, but the present subject matter is not so limited. Other optical sensors can be used. The sensor fields can include position sensitive diodes ("PSDs"), but the present subject matter is not so limited. To save cost, the illustrated embodiment uses a laser splitter to direct laser light from one laser to both sensor fields 112, 114, but the present subject matter is not so limited.

Figure 2A:
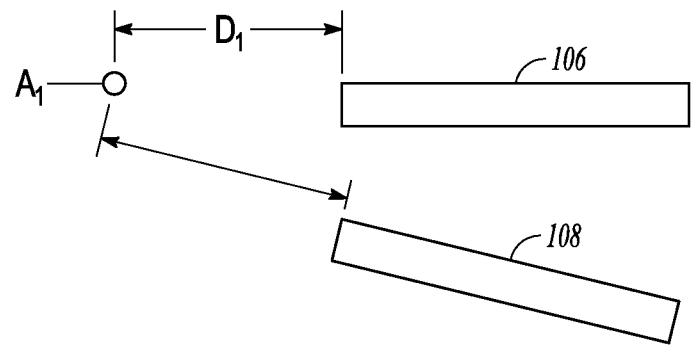
FIGS. 2A-B illustrate clutches and a condylar axis, according to some embodiments.
Figure 2B:
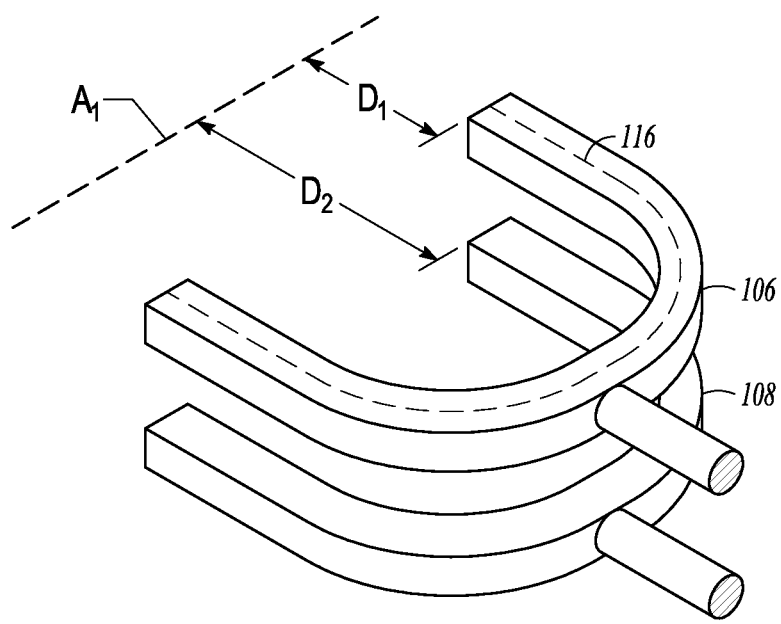

FIGS. 2A-B illustrate clutches and a condylar axis, according to some embodiments. The present subject matter accurately and precisely captures D1 and D1 by running the laser, broadcasting laser light against a sensor plane, and digitizing and storing the information captured digitally in a measurement computer for analysis and display.

Figure 3A:
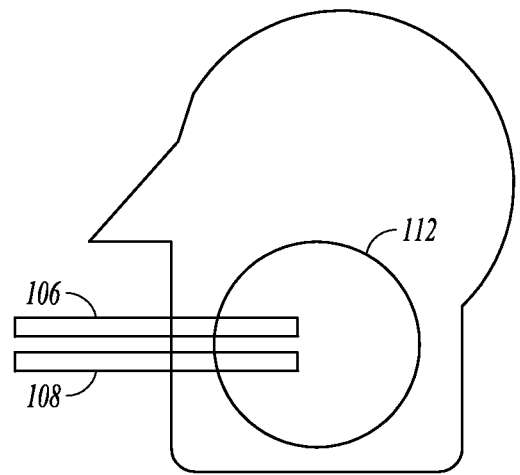
FIGS. 3A-C show a pantograph in two separate positions.
Figure 3B:
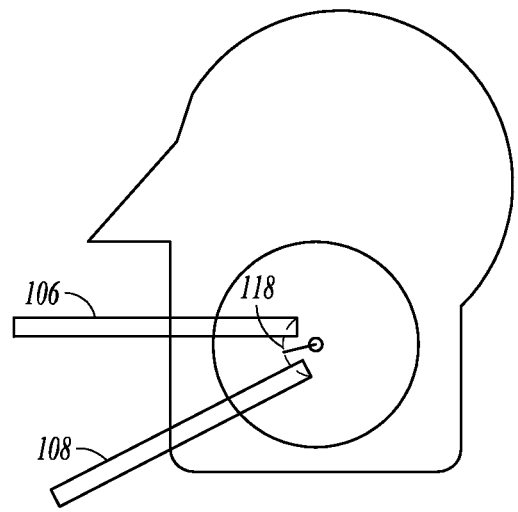
Figure 3C:
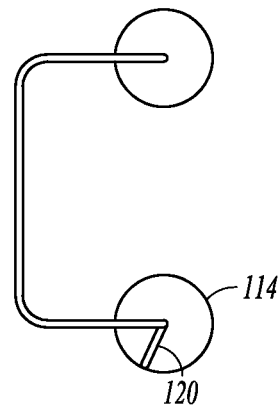

FIGS. 3A-B show a pantograph in tow separate positions. As the patient moves their mandibles from the position illustrated in FIG. 3A to the position illustrated in FIG. 3B, the lasers trace a path 118 of laser light against a plurality of sensor planes, and this path is captured digitally. The precision is to at least 0.0001 of an inch. This path can be in the anterior-posterior/dorsal-ventral plane, and/or it can be in the anterior-posterior/left-right plane, as illustrated by the path 130 traced in FIG. 3C. This is an improvement over systems that use styluses and pens which have to be changed after each recording. This approach allows for iterative captures, which can statistically improve certainty that the path of interest is desired. This information is used to study the patient and to provide therapy to the patient. In some embodiments, a measurement computer monitors data and issues an alert to a care provider when a specific degree of statistical certainty so to the arc of the jaw is determined.

Figure 4:
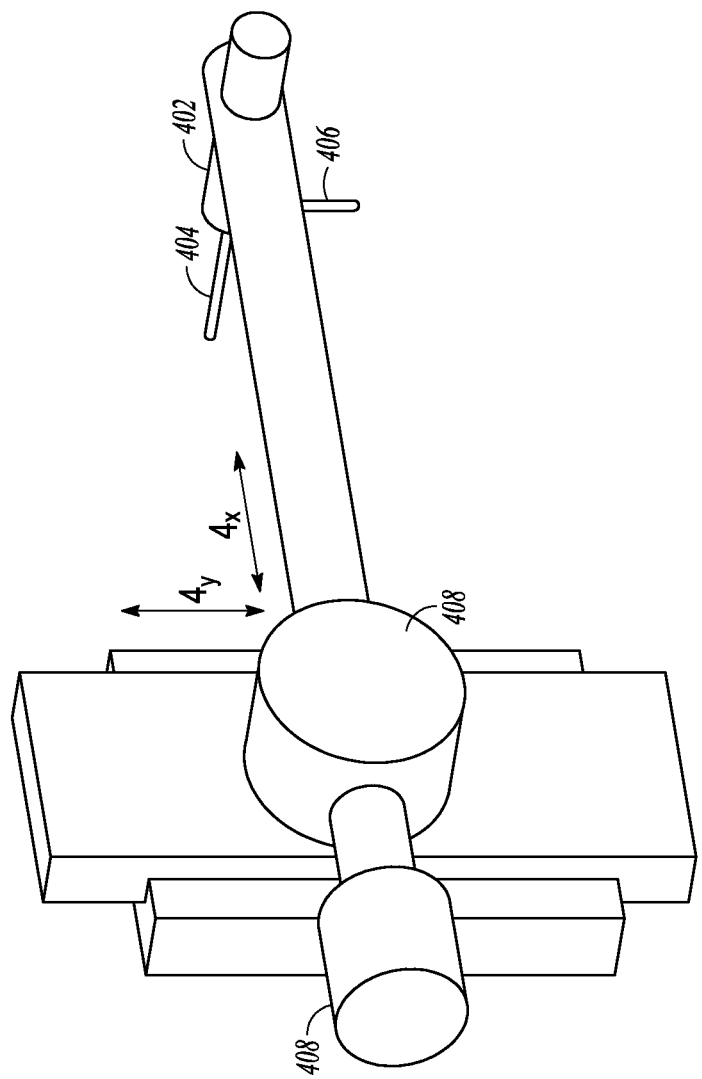
FIG. 4 illustrates a portion of a pantograph that includes a laser 402 that is split into a first beam 404 parallel the left-right axis, and a second beam 406 parallel the dorsal-ventral axis, according to some embodiments.

FIG. 4 illustrates a portion of a pantograph that includes a laser 402 that is split into a first beam 404 parallel the left-right axis, and a second beam 406 parallel the dorsal-ventral axis. Adjustments can be made using one or more thumb screws (or some analog) to move the laser in relation to a second pantograph along one or both of the 4X axis and the 4Y axis.

Axis of Rotation, Excursions, "Natural Path"

One procedure contemplated herein studies mandibular function. This procedure is useful to understand the bite bath as mandated by the condyle, and not the teeth. This "natural path" is the path that would be experienced but for teeth interfering with the bite.

During approximately 20 to 25 mm of opening or closing of the mouth from and to contact of the teeth, the mandible rotates around an axis of rotation A1, which is located in the condyle. This is often referred to as a "hinge movement," and therefore, this axis is called the "hinge axis." When the condyles are in their anterior-superior, "seated" position in the mandibular fossae, this axis is called the "terminal hinge axis." This is understood to be the physiologic position from which "mandibular movements" or "excursions" start. A "mandibular movement" might be opening the mouth, moving the mandible in an anterior direction or moving the mandible in a right or left excursive movement.

The teeth of some patients are arranged such that when they bite in their normal, day to day occlusion (intercuspal position or habitual occlusion), the condyles are in the normal, anterior-superior location in the mandibular fossa and therefore, the axis of rotation is also in the normal location. However, one problem is that the teeth of some patients are arranged such that when they bite in their normal day-to-day occlusion, the condyles are not in the anterior-superior location in the mandibular fossae, and therefore the axis of rotation is at some variance from that which is considered physiologic.

The problem noted above becomes more obvious when the person experiences a related "problem" in the form of "muscle splinting" or cramping. When the occlusion is not in harmony with the physiologic position of the condyles, the muscles must move the mandible to the position where their teeth will bite in their normal day today bite (habitual occlusion). If the muscle activity is beyond their capacity to tolerate this function, they start to hurt.

A second problem occurs if the person's axis of rotation is located at some variance from the desired location. When the mandible is moved in a lateral excursion, the patient moves in a habitual pathway that works. The muscles navigate the mandible in the pathway in which "interferences" or obstacles do not occur. However, during sleep or at various times such as resting with the teeth slightly apart, the condyles tend to seat in their physiologic position, and then when the mandible moves in an excursion, or the "natural path," a problem occurs in that the teeth experience "interferences," or problematic tooth contacts. This results in abnormal tooth wear, called "facets." If severe, these interferences result in bone loss, a need for a "root canal treatment," muscle splinting, temporomandibular joint disorders and other problems. Patients attempt to counter these afflictions through habitual adaptation, i.e. muscle training.

A problem also can occur during the treatment process of fabricating and placing a prosthetic dental item, such as a crown or a bridge. If the occlusal (biting surface of a tooth) surface of a gold or porcelain crown is not designed and formed in a manner that provides for both the habitual and physiologic (natural) function, the patient may experience difficulty in the form of tooth pain, muscle pain, tm joint paint and headaches. Therefore, in addition to simple day-to-day function problems, there is the potential for treatment problems if a dental provider does not address the matters of axis of rotation and excursive mandibular movement.

If a dental provider is treating the entire occlusion, then it is mandatory that the axis of rotation, or hinge axis is located, recorded and transferred to an appropriate instrument on which the prosthetic item is to be fabricated. The present subject matter performs this function.

Some instruments do not locate the axis of rotation accurately and are difficult and time consuming to use. In addition, quite often an instrument is used to determine an "arbitrary" or "estimated" axis of rotation. In this method, some device is used to locate a point 13 mm anterior to the tragus of the ear on a line from the tragus to the outer canthus of the eye. This has been determined to approximate the location of the axis of rotation. The problem is that this is only a poor estimation of the actual axis of rotation, and it could vary from one-half a millimeter to two or three millimeters. There will always be some degree of error when an "estimated axis" is used. Therefore, it is critical to accurately locate the physiologic axis of rotation when treating the entire occlusion with a full-mouth reconstruction, orthodontic treatment or any treatment that involves the entire occlusion. Known solutions are inaccurate, difficult to use and consume an inordinate amount of time in use. The present subject matter addresses these problems.

One way the present subject matter addresses these problems is by allowing the care provider to understand the natural path and the habitual path in operation of an articulator. The present subject matter, through tooth scans, can digitize bite motion and store and display that on a measurement computer, in conjunction with an actual bite. This could be done by replacing the adjusters 150 with linear distance monitors. Then a measurement computer would have scanned teeth and would understand the bite via data received from the system 100.

The present subject matter additionally allows modeling of natural path and habitual path via an 3D bench top articulator. This articulator, as disclosed herein in relation to various embodiments, uses servo motors to move the mandibles in relation to one another to simulate a bite via the methods set out above.

Centric Relation Bite Registration

If the patient has soreness or pain in the muscles of mastication or if the patient has a temporomandibular ("TM") joint disorder, one should resolve those problems prior to attempting to accomplish a centric relation bite registration. One can to the bite registration, but it most likely will not be accurate.

The process for resolving muscle soreness or pain or symptoms of a TM joint disorder may involve the use of an occlusal splint (a plastic device that fits over the teeth to provide proper occlusion function in order to allow healing) for several months. Other measures such as physical therapy may be involved as well.

If the patient does not have soreness or pain of the muscles of mastication and does not have a TM joint disorder or if the patient has had these problems resolved, then one proceeds with the bite registration, which is described below.

In using the anterior stop technique, one can prepare a four thickness piece of occlusion wax that provides for the width of the maxillary anterior teeth and that provides for contact with the mandibular incisors. Generally, this piece of wax will be 1½ inches long, ½ to ¾ inches wide and ½ inches deep. Heat the wax in a water bath at 140 degrees.

Prepare a two thickness piece of occlusion wax (the posterior piece) that provides for the width of the maxillary first molars at their buccal surface. Generally, this piece of wax will be 3 to 4 inches long, 1 inch wide and ⅜ inches deep. Heat the wax in a water bath at 140 degrees.

Attached the system 100 to the patient. After instruction the patient regarding the procedure, place the dead soft anterior piece of wax on the maxillary anterior teeth. With the thumb on the patient's chin, the index finger under the left gonial angle of the mandible and the middle finger under the right gonial angle of the mandible, manipulate the patient's mandible to cause an arcing motion of four to eight millimeters while applying only an upward pressure at the gonial angles. As this is being accomplished, one should feel the mandible seating in "rest position," or that position of the mandible one would find it to be when the muscles of mastication are not active. The purpose of the upward pressure is only to sense if the patient moves the mandible out of rest position. The manipulation must start at rest position and the condyles must not be allowed to move out of their seated position. As this is being accomplished, one will note a smooth and freely arcing motion to the mandible. The patient is instructed to let the lower incisors strike the wax. Then the patient is instructed to "squeeze" and "bite slowly." The care provider instructs the patient to stop biting when the maxillary and mandibular posterior teeth are about 1½ to 2 millimeters from contact. The posterior teeth cannot contact at any point or the patient will move the mandible to their habitual occlusion and the bite registration is invalid. If the procedure is satisfactory, the anterior wax piece is cooled with air from an air syringe, the piece is held in place while the patient is instructed to open, and the wax piece is place in ice water.

After the anterior wax piece has hardened in the ice water, the dead soft posterior wax piece is placed on the maxillary first molars, extending across the palate. The wax is pressed onto the occlusal surface and held in place. Then the cold, hard anterior wax piece is replaced on the maxillary anterior teeth.

Optionally, the wax is coupled to the clutches 104, 106 so that the system 100 can record the relation of the teeth to the axis when the system is engaged to record. One input to record could be a foot pedal, but the present subject matter is not so limited.

During a recording period, the care provider places the fingers on the chin and the gonial angles as before and manipulates the mandible in the same manner, watching carefully to be certain the mandibular incisors fit into the registration imprints in the wax.

If the incisors fit, during another recording period, the patient is told to "squeeze" and then "bite hard evenly on both sides." During this biting, the muscles of mastication (primarily the masseter and internal ptyergoid muscles) seat the condyles in a physiologic, seated position, which is understood to be in a superoanterior location in the mandibular fossae. This position can be recorded.

The posterior wax piece is cooled with air from the air syringe, the posterior piece is held against the maxillary molars and the patient is instructed to "open." The anterior and posterior wax pieces are floated in water to prevent distortion. The centric relation wax bite registration (2 pieces) together with a proper transfer of the condylar axis via the system 100 are used to mount the dental models in one or more dental articulators.

Centric relation is defined as the relative location of the mandible when the condyles and their properly attached articular discs are actively positioned by the closing musculature against the superoanterior areas of the posterior slopes of the articular eminences of the mandibular fossae and are also physiologically positioned transversely.

The models are "mounted in centric relation." This is an improved mount. When combined with the improved determination of the condylar axis as set out herein, including but not limited to excursion and path data from the system 100, superior and highly accurate and precise representation on an articulator can take place.

Systems and Methods for Recording Mandibular Movement

A care provider can select clutches, upper, and lower. The care provider can fill upper and lower clutches with medium such as a wax. The care provider can fit the clutches to respective teeth. In optional embodiments, the care provider can align right and left sensor ear canal indicators to ear canals. In some embodiments, the care provider can fit lower clutch in alignment to upper clutch. In some embodiments, the care provider can fasten upper face bow to upper clutch, aligning in a horizontal plane. In some embodiments, the care provider can fasten lower face bow to lower clutch, aligning in a horizontal plane. In optional embodiments, the care provider can align right and left lasers to indicators.

In various embodiments, the care provider can power on a measurement computer, upper face bow and lower face bow and check all lasers and PSD sensors function and wireless communication with the measurement computer. In some embodiments, the care provider can position a patient in chair in upright sitting position. In some embodiments, the care provider can instruct patient to make random movement to test system function. In some embodiments, the care provider can have patient open and close their jaw several times while recording using the laser. In some embodiments, the care provider can check to see if hinge recordings, right and left sensors overlap. If not, in some embodiments, the care provider can optionally erase recordings and repeat hinging until the recordings overlap. The care provider may be able to erase recordings and repeat hinge only once. The system can optionally calibrate so that the hinge arcs substantially overlap (e.g., less than 5% different in amplitude along arc).

In various embodiments, the care provider can check arcs described by laser-on-sensors on, for example, a monitor. The arcs could optionally be stored in a memory for use by another device, such as a processor in a Mandibular Movement Simulator ("MMS") computer, as disclosed herein. In some embodiments, the care provider can query the measurement computer to show origin of arc radii with, for example, a blinking dot or target. In some embodiments, the care provider can repeat operation with different color dot to confirm duplicate result. The measurement computer could also duplicate the result or calculate statistical certainty via a number of iterations.

In some embodiments, the care provider can reposition horizontal laser beams, right, and left, to arc radii origins, as indicated and verified by the measurement computer. In some embodiments, the care provider can reposition vertical sensors on right and left sides of pantograph to align axial centers on sensors, to be coaxial with laser beams as indicated and verified on the measurement computer display and/or via a reoccurring sound that increases in frequency as the tool is moved into adjustment. In some embodiments, the care provider can choose to magnify result on monitor, and query the measurement computer if any errors, or anomalies are indicated. If there are anomalies, the care provider could store them with a flag. If they do not, the care provider may have the patient make several protrusive movements while recording, and save those recordings.

In various embodiments, the care provider may have patient make several passes of right excursive movement, while recording. Optionally, they can check if recordings overlap. If they do not, the care provider can troubleshoot by checking equipment and adjusting or calibrating either the sensors in relation to one another or the pantograph in relation to the patent. The care provider can optionally make a note and save that note in relation to the record. Also, they can have patient make several passes of left excursive movement, while recording. The care provider may check if recordings overlap. If they do not, the care provider may troubleshoot. If they do, the care provider may note this and save the data relating to success and to the actual motion in a database in relation to the note.

The care provider may remove upper face bow, with clutch intact and set it aside. The care provider may remove lower face bow, with clutch intact and set it aside. They can take impressions of upper and lower arches. They can pour upper and lower impressions with hard stone and trim.

Jig System and Method

They can mount upper an pantograph bow to a Mandibular Movement Simulator ("MMS") mounting jig. They can mount lower pantograph bow to MMS the mounting jig. The lasers are aligned to targets (e.g., sensors) on the jig. The upper and lower pantograph bows can optionally be locked together. The care provider replaces the upper and lower clutches into respective positions in the pantographs. Use pantograph to mount upper and lower trimmed stone casts to the Mandibular Movement Simulator mounting jig. At this point, the casts are mounted in a jig, and condylar axis data is also stored on the jig. This jig could be fit to a hand articulator and used to align the casts to that articulator.

Optionally, the care provider can transfer mounted casts or molds to an MMS. This is a device that is controllable in 6 axes to simulate mandibular movement. In other words, the machine can adjust the lower mandible via servo motors. The adjustment can be along the anterior-posterior axis, around that axis, along the dorsal axis and around that axis, and along the left-right axis and around. The hinge axis is substantially parallel to the left-right axis.

The upper and lower pantographs can be attached to the jig during the transfer, or they can be used to store data relating the location of the hinge axis to the jig. Once this dimension is known, the jig can then be coupled to the MMS and the MMS can be calibrated to replicate movement according to the axis transported with the jig. This way, the care provider does not have to buy two sets of pantographs and can leave one at the measurement location and still replicate the motion at the MMS. If the care giver has one or more hand articulators, she can mount the jigs of different patients to different articulators and reconstructive work can be done for multiple patients simultaneously.

System and Method for Transfer to MMS without Jig

In an additional embodiment, one that can eliminate the error associated with transfer of the hinge axis location information from the measurement site, to a jig, and to the MMS, one can simply mount casts to the MMS, fit the pantographs to the MMS and the casts, and then have the MMS cycle through motions until it can replicate the arc data that's been stored in the measurement computer from the pantographs. It would do this using feedback. For example, if the laser does not record a path that overlaps with the stored bite path, the simulated path is adjusted, until the simulated path replicates the stored path within a specified degree of tolerance.

MMS Algorithms

The MMS is a multi-mode system. Modes are selectable by a user to perform different functions. In various embodiments, the MMS can be controlled to execute a program stored on the MMS computer to simulate natural paths. In a further mode, it can be controlled to simulate habitual paths. In a further mode, it can be controlled to find a simulated habitual path by starting with a natural path and forcing teeth to collide with one another.

In measuring bite, to find a natural path, habitual paths should be suppressed. If a patient has habitual paths, one or more of the following methods can be used to erase it from the patient's muscle memory: the patient can be numbed, or can have their jaw locked together, or their bit modified with a splint. Once the bite is restore it to a natural path, it can be recorded.

In embodiments where natural path is simulated, using the hinge axis as a reference, the MMS is operated to explore a normal range of mandibular motion. The care giver can study the look of the mold as the system ranges through this motion. Restorations can be made, and one can ensure that the natural path is preserved.

In additional embodiments, the care provider can execute a program stored on the MMS computer to find and record habitual paths. In this algorithm, the MMS attempts to move a casting through natural motions as determined during measurement. Interferences will be bumped into and recorded. The machine will attempt new paths, and can report progress to the care provider. This attempt to find new paths will simulate the patient's effort to find habitual paths.

The MMS can move the castings through a natural path set of predetermined motions to determine what the habitual path is. This can optionally be correlated with a predetermined habitual path that is measured with a wax bite or with the system 100, above.

As the habitual paths are found, the care provider can modify the teeth of the cast to eliminate the need for the habitual path. This can aid in the creation of improved restorations. The 3D nature of the process assists the care provider in modifying the casts by hand, which can save time and money. Habitual paths that are determined can be stored in the MMS computer or elsewhere for later review.

Figure 5:
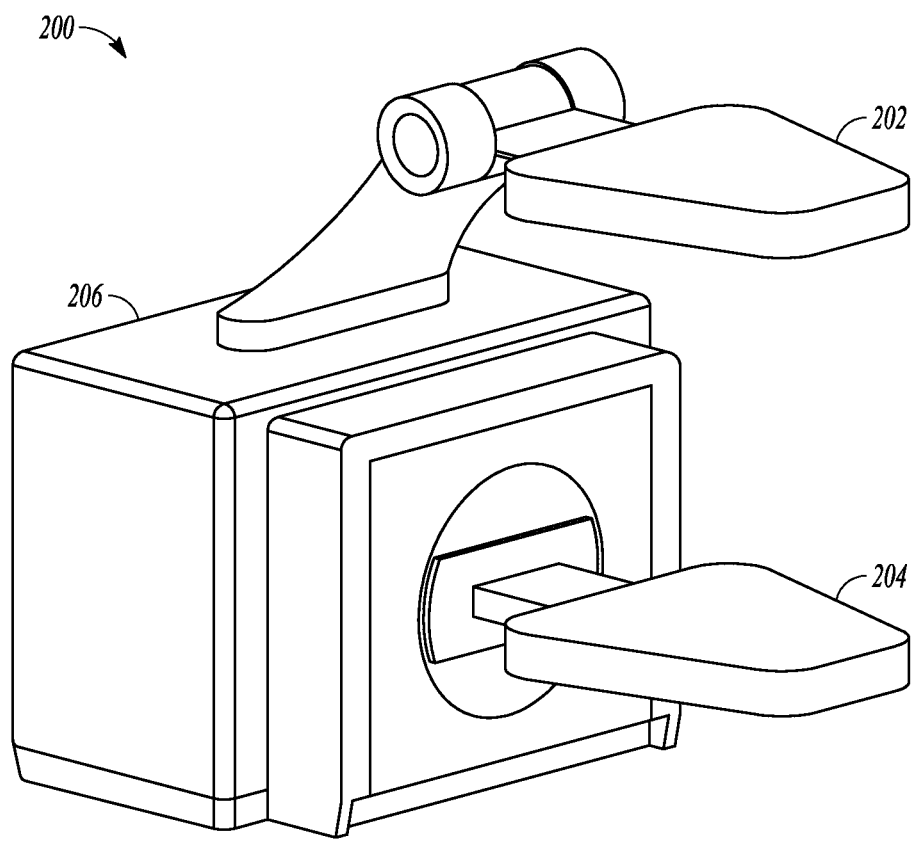
FIG. 5 illustrates an MMS 200, according to some embodiments. A cast of the top teeth is coupled to the top bad 202, according to some embodiments.

FIG. 5 illustrates an MMS 200, according to some embodiments. A cast of the top teeth is coupled to the top bad 202. A cast of the bottom teeth is coupled to the bottom pad 204. The servo box 206 contains servos to move these pads in relation to one another along up to six degrees of freedom.

Figure 6:
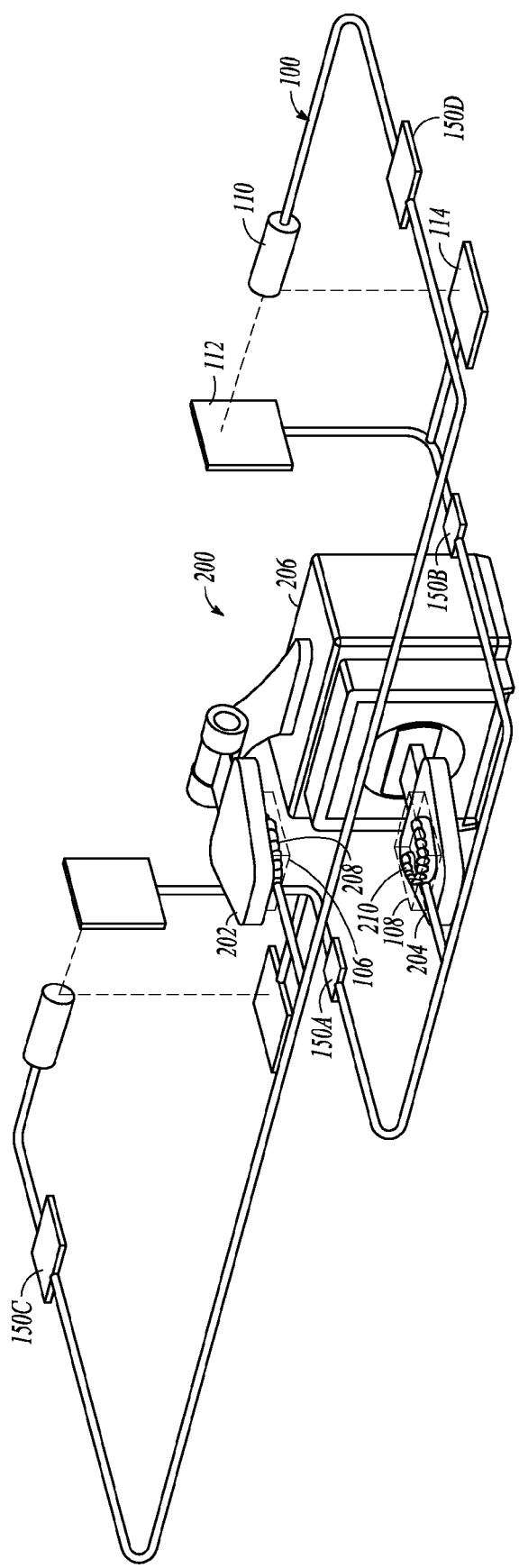
FIG. 6 illustrates an example system and method for transfer of bit information to MMS without a jig, according to some embodiments.

FIG. 6 illustrates an example system and method for transfer of bit information to MMS without a jig. In them embodiments, the system 100 is fitted to casts 208 and 210 that are coupled to the MMS. The pantographs are moved in relation to each other, and the laser 110 broadcasts a beam to sensor fields 112 and 114. The MMS can thus learn how to replicate the measured bite motion by trying to model (e.g., curve fit) data monitored from motion of the MMS to stored data, and adjusting the motion of the MMS accordingly.

Figure 7:
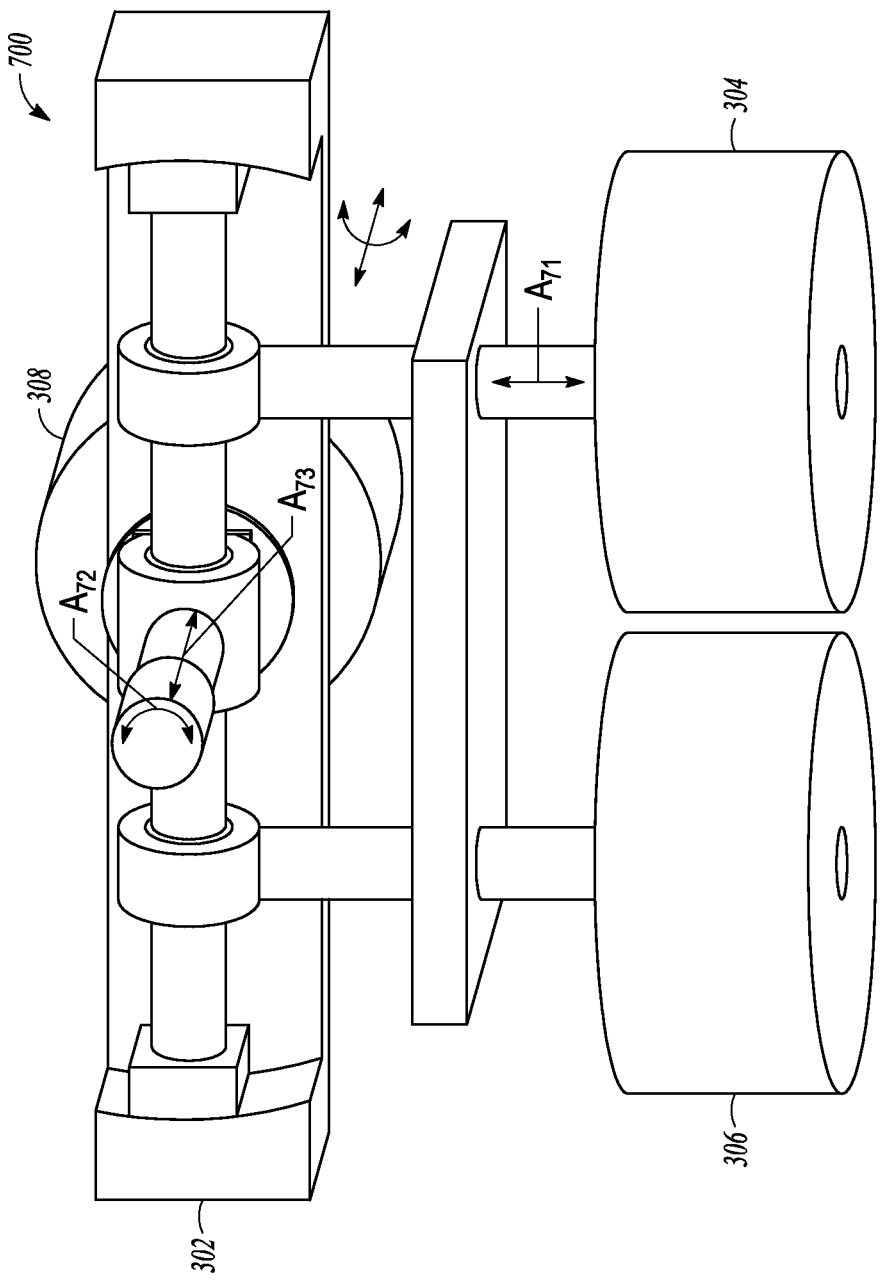
FIG. 7 illustrates a MMS, according to some embodiments.

FIG. 7 illustrates a MMS 700, according to one embodiment. The motors 304, 306 and 308 move the bottom plate, to which a cast is mounted, along A71, A72 and A73, among others. The guide 302 supports rotation. In some embodiments, the guide 302 includes a bushing.

Figure 8:
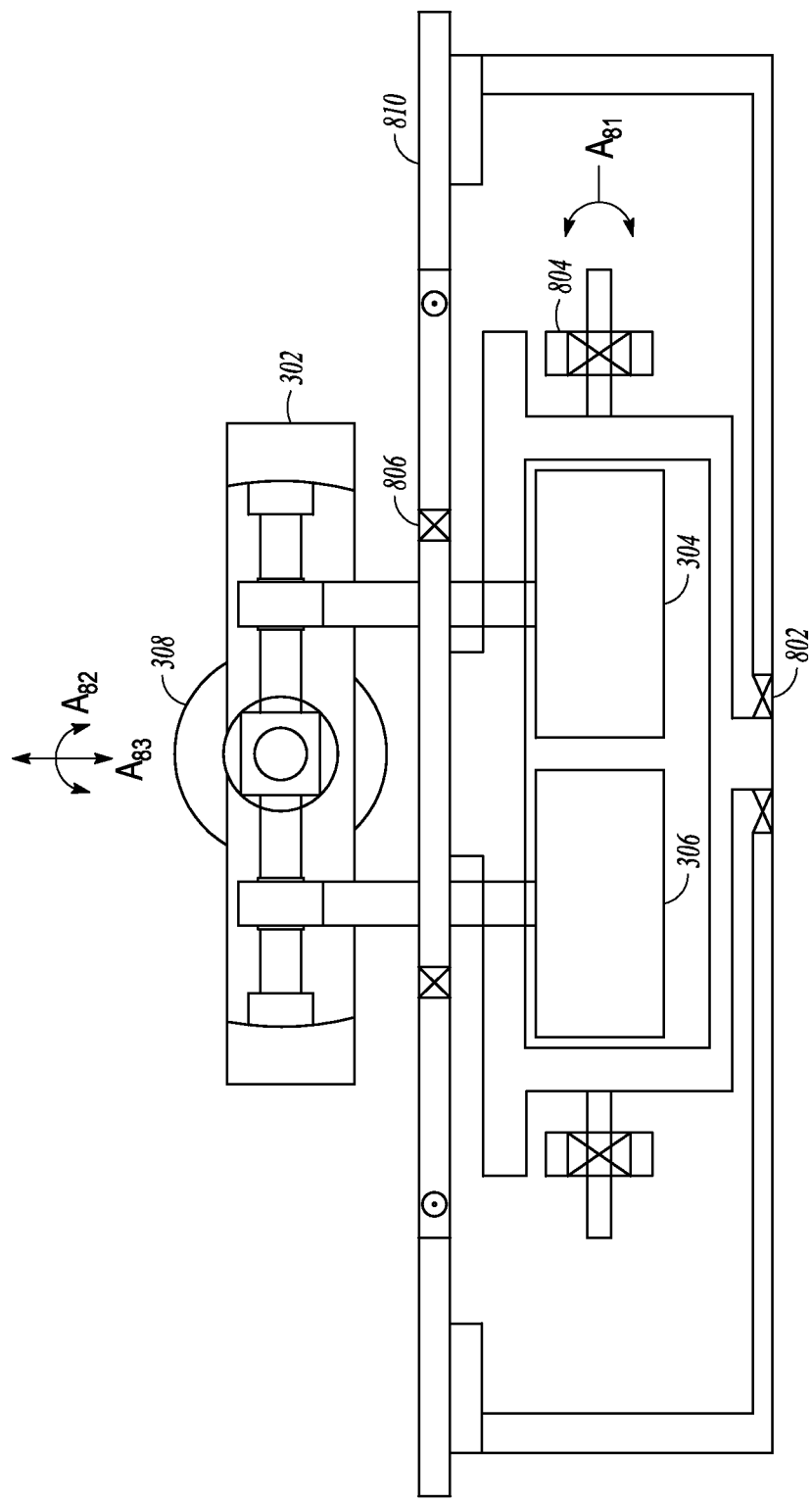
FIG. 8 shows a further portion of an MMS, according to various embodiments.

FIG. 8 shows a further portion of an MMS, according to various embodiments. The system can move at least along axis A81, A82 and A83. Bearings 802, 804 and 806 support such rotation. A fixture 810 is coupled to the MMS to provide further rotation ability.

Figure 9:
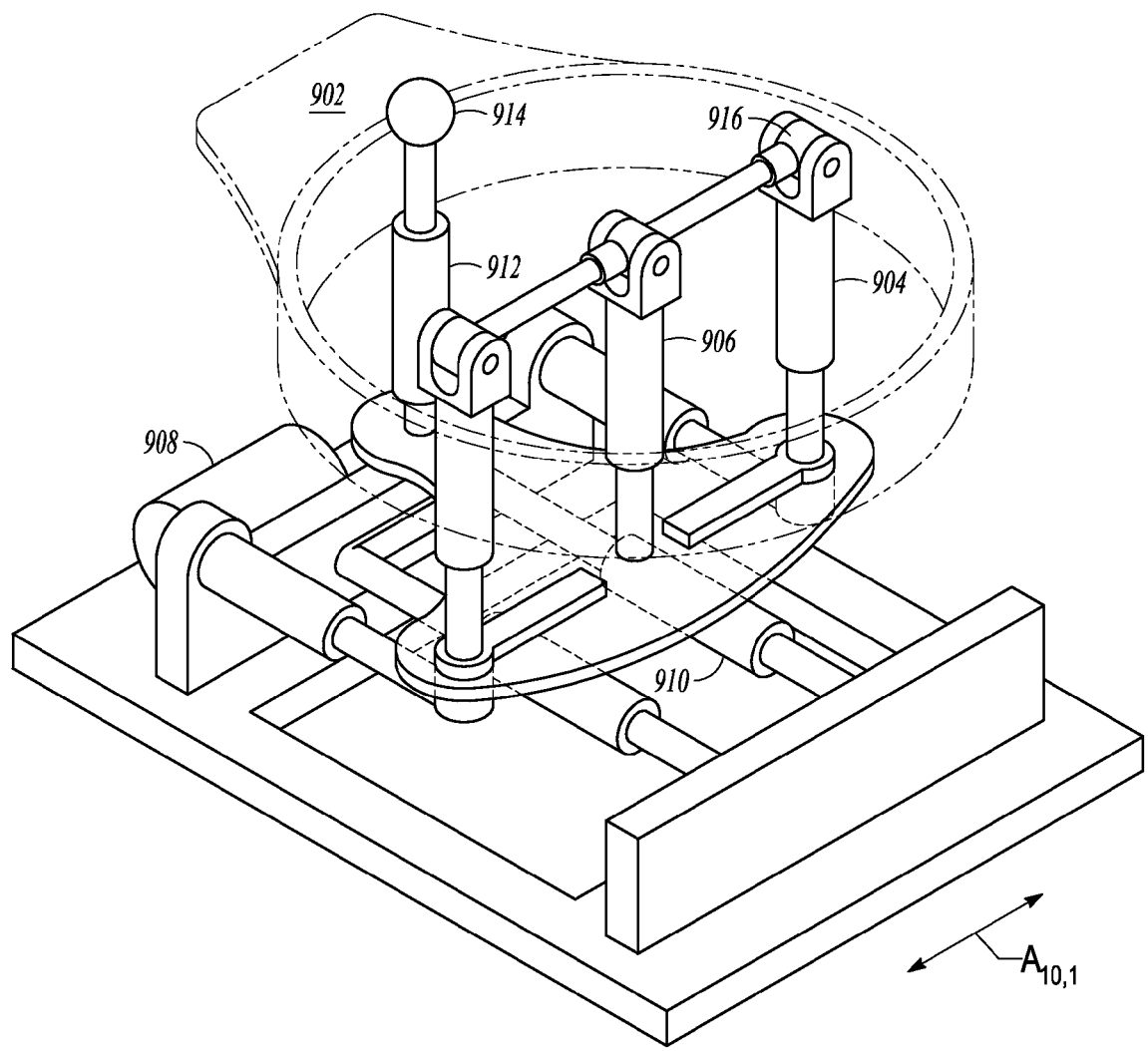
FIG. 9 illustrates a further MMS, according to some embodiments.

FIG. 9 illustrates a further MMS 900, according to some embodiments. The MMS includes linear motors 904, 906, 908 and 910. The system moves the bottom articulator plate 902, to which a cast is coupled, free to move along the six degrees of freedom discussed above. A spherical joint 914 and hinge joints 916 are coupled to the articulator plate 902 and assist in motion.

Figure 10:
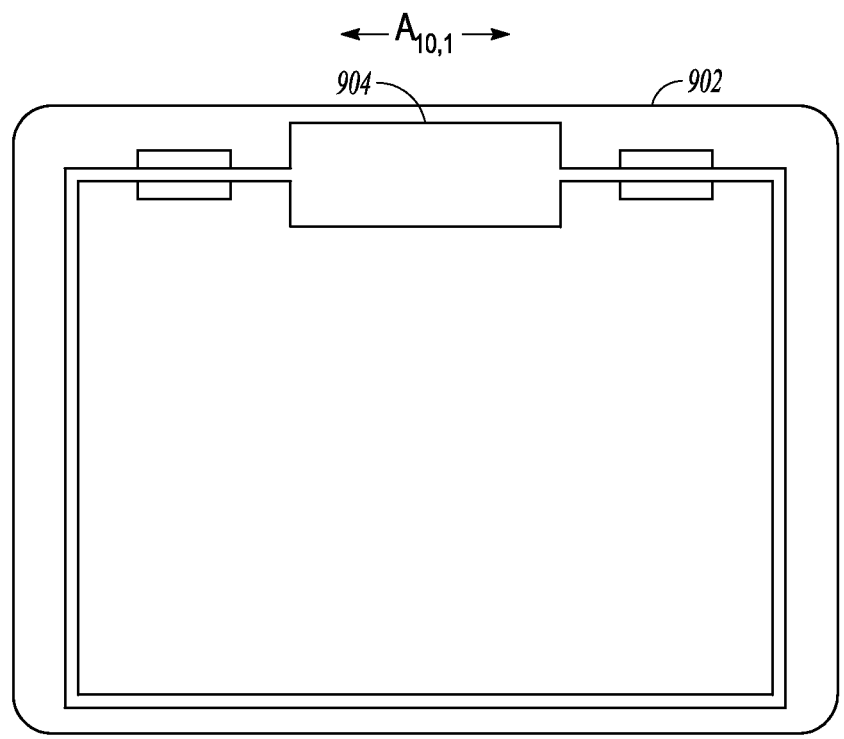
FIG. 10 illustrates a table on which the device of FIG. 9 can be mounted, to gain motion along axis A10, 1, according to some embodiments.

FIG. 10 illustrates a table on which the device of FIG. 9 can be mounted, to gain motion along axis A10, 1. Motion, in some examples, occurs via actuation of motor 904 to move along the axis. Linear motors 904 and 906 as well as hinge joints 916 are illustrated coupled to bottom plate 902.

Figure 11:
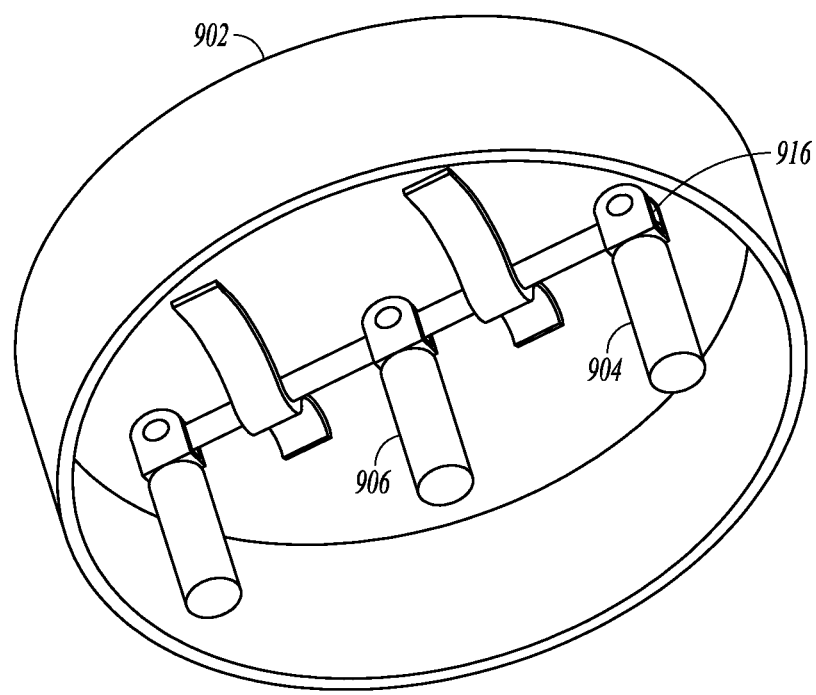
FIG. 11 is a perspective view showing the underside of a bottom articulator plate, according to some embodiments.

FIG. 11 is a perspective view showing the underside of a bottom articulator plate, according to some embodiments. The general concavity of the bottom plate 902, on a side not shown, is further illustrated.

Figure 12:
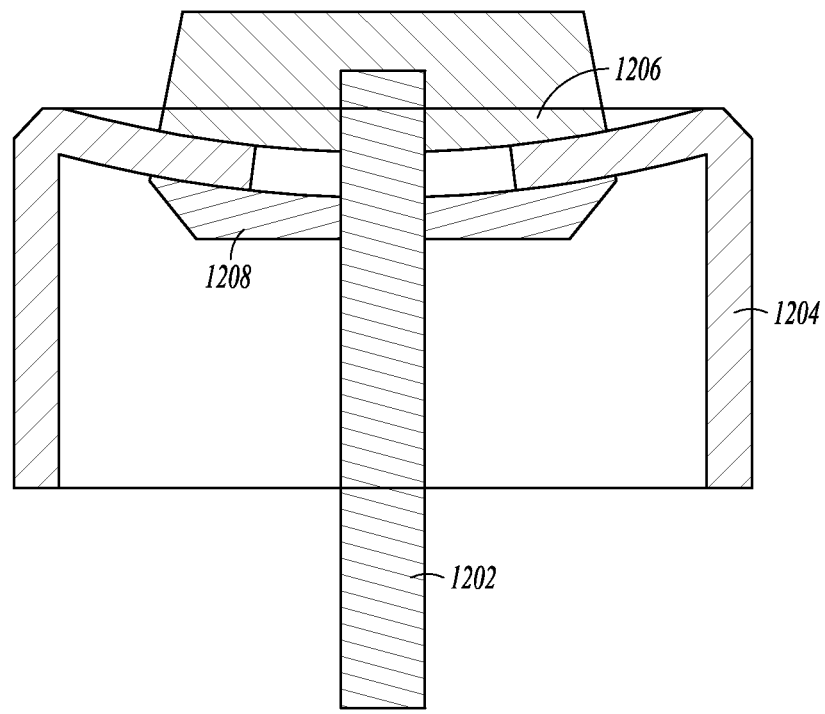
FIG. 12 illustrates a further MMS, according to some embodiments.

FIG. 12 illustrates a further MMS, according to some embodiments. The device is show in cross section. In some embodiments, the device is symmetrical about the cross section. A tilt shaft 1202 can move in relation to support ring 1204 to adjust the mount plate 1206 in relation to the support ring 1204. In various embodiments, a capture plate 1208 is to pinch the support ring by drawing the mount plate 1206 to the capture plate 1208, with the support ring in the middle. In various embodiments, the support ring has a concavity to contain the mount plate, to which a cast is coupled. Accordingly, the support ring 1204 is shaped like a sphere portion, and the mount plate 1206 and capture plate 1208 are conformed to the support ring 1204 to slide along the support ring 1204 while maintaining contact with the support ring.

Figure 13:
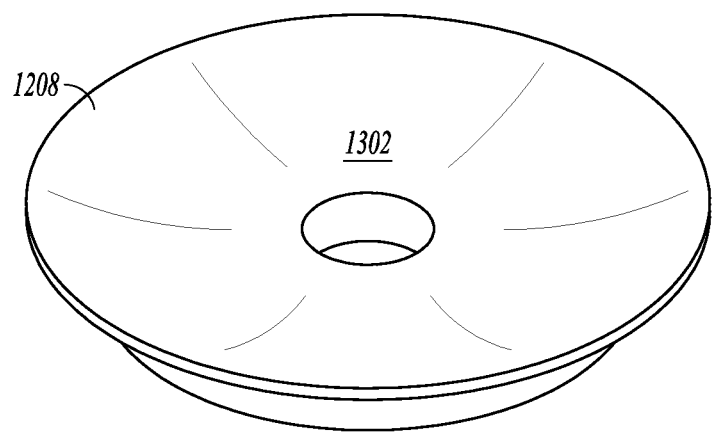
FIG. 13 illustrates a perspective view of the capture plate 1208, according to some embodiments.

FIG. 13 illustrates a perspective view of the capture plate 1208, according to some embodiments. The support ring's concavity 1302 is shown.

The tilt shaft 1202 can optionally be threaded, with the capture plate 1208 threaded onto the tilt shaft 1202. FIGS. 12-16 illustrate further views of the components of FIG. 12.

Figure 14:
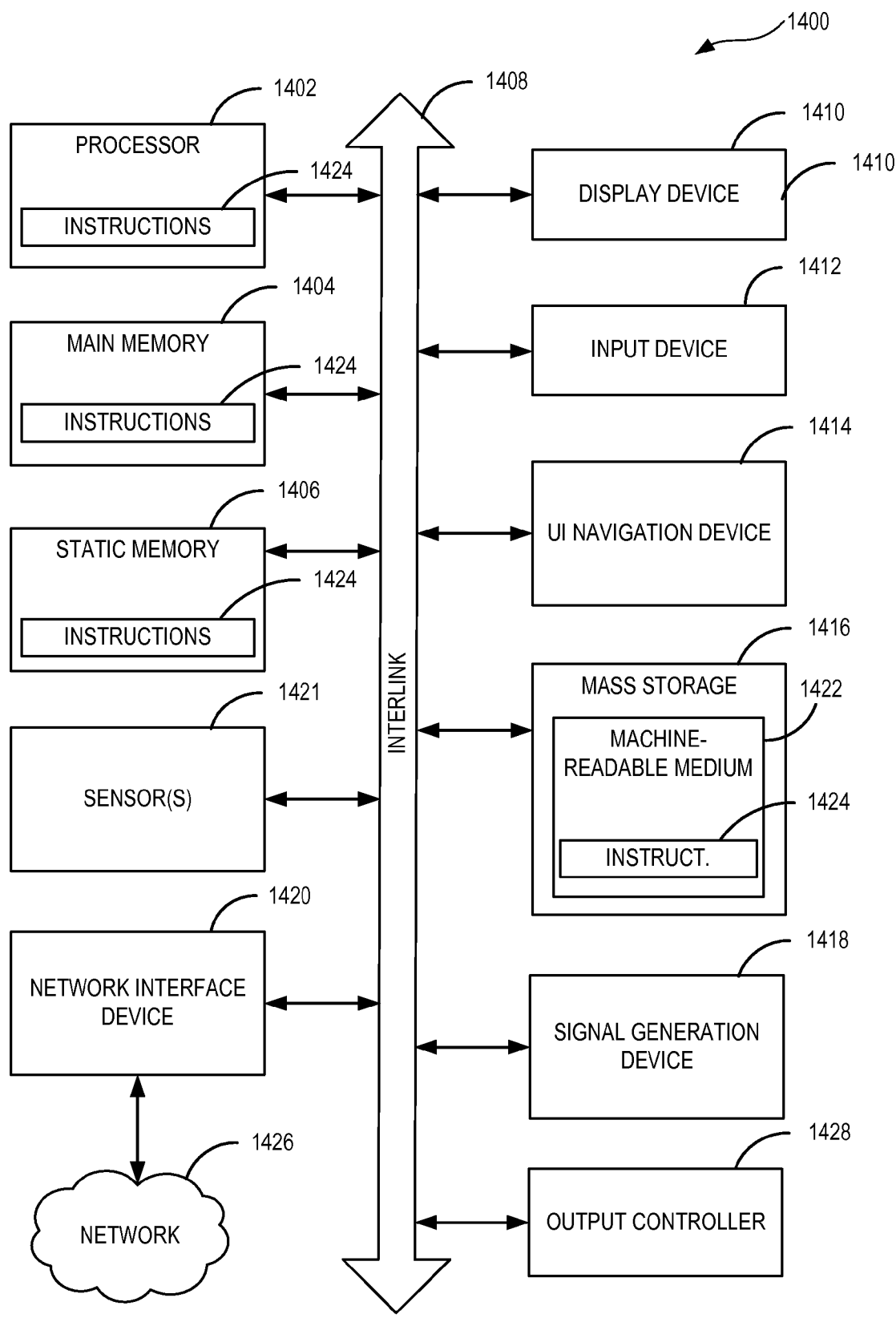
FIG. 14 is a block diagram illustrating an example of a machine upon which one or more embodiments may be implemented.

FIG. 14 illustrates a block diagram of an example circuit 1400 which can be used in conjunction with any of the examples discussed herein. The circuit 1400 can operate as a standalone device or can be connected (e.g., networked) to other circuits. The circuit 1400 can form all or a part of a personal computer (PC), a tablet PC, a set-top box (STB), a Personal Digital Assistant (PDA), a mobile telephone, a web appliance, a network router, switch or bridge, or any machine capable of executing instructions (sequential or otherwise) that specify actions to be taken by that machine. The term "circuit" can include any collection of circuits that individually or jointly execute a set (or multiple sets) of instructions to perform any one or more of the systemologies discussed herein, such as cloud computing, software as a service (SaaS), other computer cluster configurations. Insofar as circuit embodiments include software, such software can reside on a machine readable medium. Software, when executed by hardware, can cause the hardware to perform a function.

Circuit (e.g., computer system) 1400 can include a hardware processor 1402 (e.g., a central processing unit (CPU), a graphics processing unit (GPU), a hardware processor core, or any combination thereof), a main memory 1404 and a static memory 1406, some or all of which can communicate with each other vian an interlink (e.g., bus) 1408. The circuit 1400 can further include a display unit 1410, an alphanumeric input device 1412 (e.g., a keyboard), and a user interface (UI) navigation device 1414 (e.g., a mouse). The display unit 1410, input device 1412 and UI navigation device 1414 can be a touch screen display. The circuit 1400 can additionally include a storage device (e.g., drive unit) 1416, a signal generation device 1418 (e.g., a speaker), a network interface device 1420, and one or more sensors 1421, such as a global positioning system (GPS) sensor, compass, accelerometer, or other sensor. The circuit 1400 can include an output controller 1428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1416 can include a machine readable medium 1422 on which is stored one or more sets of data structures or instructions 1424 (e.g., software) embodying or utilized by any one or more of the techniques or functions described herein. The instructions 1424 can also reside, completely or at least partially, within the main memory 1404, within static memory 1406, or within the hardware processor 1402 during execution thereof by the circuit 1400. In an embodiment, one or any combination of the hardware processor 1402, the main memory 1404, the static memory 1406, or the storage device 1416 can constitute machine readable media.

While the machine readable medium 1422 is illustrated as a single medium, the term "machine readable medium" can include a single medium or multiple media (e.g., a centralized or distributed database, and/or associated caches and servers) that configured to store the one or more instructions 1424.

The term "machine readable medium" can include any medium that is capable of storing, encoding, or carrying instructions for execution by the circuit 1400 and that cause the circuit 1400 to perform any one or more of the techniques of the present disclosure, or that is capable of storing, encoding or carrying data structures used by or associated with such instructions. Non-limiting machine readable medium embodiments can include solid-state memories, and optical and magnetic media. In an embodiment, a massed machine readable medium comprises a machine readable medium with a plurality of particles having resting mass. Specific embodiments of massed machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1424 can further be transmitted or received over a communications network 1426 using a transmission medium via the network interface device 1420 utilizing any one of a number of transfer protocols (e.g., frame relay, internet protocol (IP), transmission control protocol (TCP), user datagram protocol (UDP), hypertext transfer protocol (HTTP), etc.). Embodiment communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), peer-to-peer (P2P) networks, among others. The network interface device 1420 can include one or more physical jacks (e.g., Ethernet, coaxial, or phone jacks) or one or more antennas to connect to the communications network 1426. The network interface device 1420 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the circuit 1400, and includes digital or analog communications signals or other intangible medium to facilitate communication of such software.

The example circuit 1400 can include a digital bite replicator. The example circuit 1400 can include a computer such as to store a measured distance. Sensors 1421 can include sensors 110 in FIG. 1. Examples herein provide a digital dental diagnostic system.

Figure 15:
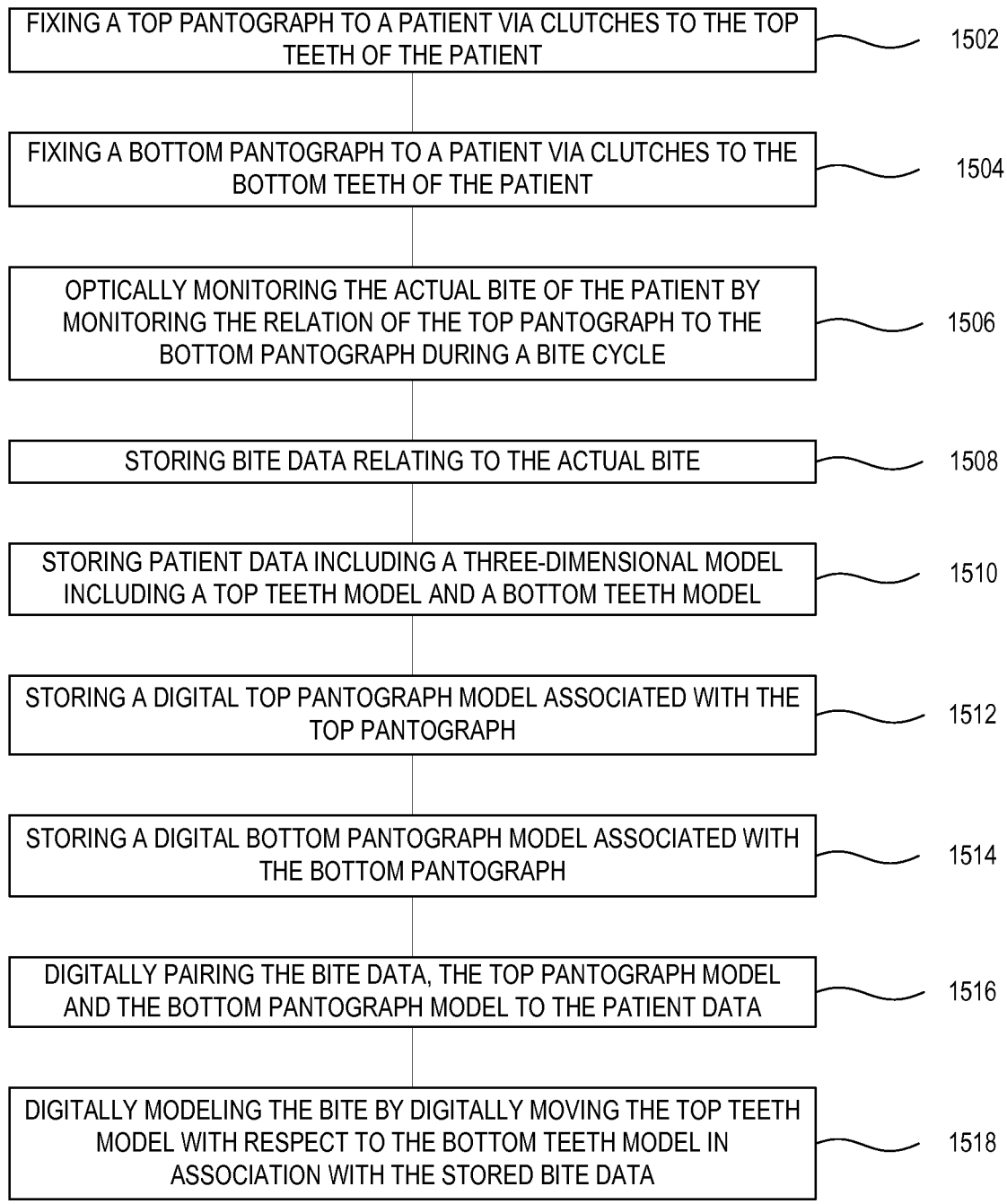
FIG. 15 is a method of modeling a bite, according to an example.

FIG. 15 is a method 1500 of modeling a bite, according to an embodiment. At 1502, the method can include fixing a top pantograph to a patient via clutches to the top teeth of the patient. At 1504, the method can include fixing a bottom pantograph to a patient via clutches to the bottom teeth of the patient. At 1506, the method can include optically monitoring the actual bite of the patient by monitoring the relation of the top pantograph to the bottom pantograph during a bite cycle. At 1508, the method can include storing bite data relating to the actual bite. At 1510, the method can include storing patient data including a three-dimensional model including a top teeth model and a bottom teeth model. At 1512, the method can include storing a digital top pantograph model associated with the top pantograph. At 1514, the method can include storing a digital bottom pantograph model associated with the bottom pantograph. At 1516, the method can include digitally pairing the bite data, the top pantograph model and the bottom pantograph model to the patient data. At 1518, the method can include digitally modeling the bite by digitally moving the top teeth model with respect to the bottom teeth model in association with the stored bite data.

Figure 16:
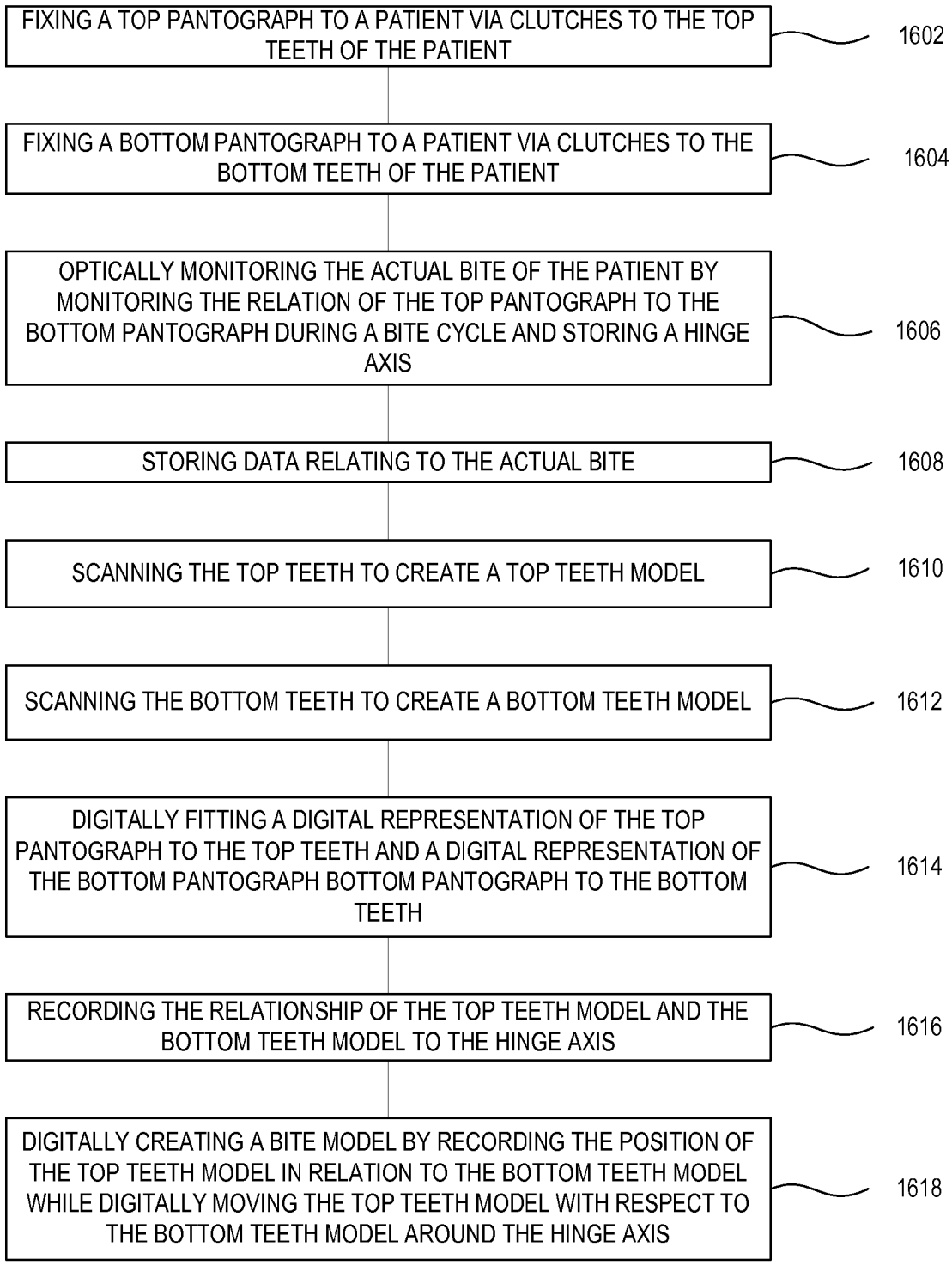
FIG. 16 is a method of creating a bite model, according to an example.

FIG. 16 is a method 1600 of creating a bite model, according to an embodiment. At 1602, the method can include fixing a top pantograph to a patient via clutches to the top teeth of the patient. At 1604, the method can include fixing a bottom pantograph to a patient via clutches to the bottom teeth of the patient. At 1606, the method can include optically monitoring the actual bite of the patient by monitoring the relation of the top pantograph to the bottom pantograph during a bite cycle and storing a hinge axis. At 1608, the method can include storing data relating to the actual bite. At 1610, the method can include scanning the top teeth to create a top teeth model. At 1612, the method can include scanning the bottom teeth to create a bottom teeth model. At 1614, the method can include digitally fitting a digital representation of the top pantograph to the top teeth and a digital representation of the bottom pantograph bottom pantograph to the bottom teeth. At 1616, the method can include recording the relationship of the top teeth model and the bottom teeth model to the hinge axis. At 1618, the method can include digitally creating a bite model by recording the position of the top teeth model in relation to the bottom teeth model while digitally moving the top teeth model with respect to the bottom teeth model around the hinge axis.

Optional methods can include replicating the actual bite digitally using feedback by comparing the bite data relating to the actual bite to the modeled bite. Optional methods can include storing the bite data includes communicating the bite data wirelessly to a measurement computer and storing the data therein. Optional methods can include storing a scan of the top teeth and the bottom teeth in the measurement computer. Optional methods can include storing a scan of the top pantograph and the bottom pantograph. Optional methods can include displaying the bite on a display of the measurement computer. A display can include output readable by a computer. A display can include a visible display such as a video screen. Optional methods can include detecting a bite anomaly with the measurement computer. Optional methods can include flagging the bite anomaly and displaying the flag. Optional methods can include controlling an automatic articulator with the measurement computer.

The above detailed description includes references to the accompanying drawings, which form a part of the detailed description. The drawings show, by way of illustration, specific embodiments in that may be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "An and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate

What is claimed is:

1. A method, comprising:
fixing a top pantograph to a patient via clutches to the top teeth of the patient;
fixing a bottom pantograph to a patient via clutches to the bottom teeth of the patient;
optically monitoring the actual bite of the patient by monitoring the relation of the top pantograph to the bottom pantograph during a bite cycle;
storing bite data relating to the actual bite;
storing patient data including a three-dimensional model including a top teeth model and a bottom teeth model;
storing a digital top pantograph model associated with the top pantograph;
storing a digital bottom pantograph model associated with the bottom pantograph;
digitally pairing the bite data, the top pantograph model and the bottom pantograph model to the patient data; and
digitally modeling the bite by digitally moving the top teeth model with respect to the bottom teeth model in association with the stored bite data.

2. The method of claim 1, comprising replicating the actual bite digitally using feedback by comparing the bite data relating to the actual bite to the modeled bite.

3. The method of claim 1, wherein storing the bite data includes communicating the bite data wirelessly to a measurement computer and storing the data therein.

4. The method of claim 3, comprising storing a scan of the top teeth and the bottom teeth in the measurement computer.

5. The method of claim 4, comprising displaying the bite on a display of the measurement computer.

6. The method of claim 4, comprising storing a scan of the top pantograph and the bottom pantograph.

7. The method of claim 3, including detecting a bite anomaly with the measurement computer.

8. A method, comprising:
fixing a top pantograph to a patient via clutches to the top teeth of the patient;
fixing a bottom pantograph to a patient via clutches to the bottom teeth of the patient;
optically monitoring the actual bite of the patient by monitoring the relation of the top pantograph to the bottom pantograph during a bite cycle and storing a hinge axis;
storing data relating to the actual bite;
scanning the top teeth to create a top teeth model;
scanning the bottom teeth to create a bottom teeth model;
digitally fitting a digital representation of the top pantograph to the top teeth and a digital representation of the bottom pantograph bottom pantograph to the bottom teeth;
recording the relationship of the top teeth model and the bottom teeth model to the hinge axis;
digitally creating a bite model by recording the position of the top teeth model in relation to the bottom teeth model while digitally moving the top teeth model with respect to the bottom teeth model around the hinge axis.

9. The method of claim 8, comprising storing a scan of the top teeth and the bottom teeth in a measurement computer.

10. The method of claim 9, comprising displaying the bite on a display of the measurement computer.

11. The method of claim 9, including detecting a bite anomaly with the measurement computer.

12. The method of claim 11, comprising flagging the bite anomaly and displaying the flag.

13. The method of claim 9, comprising controlling an automatic articulator with the measurement computer.

14. A system for modeling the bite of a digital top teeth model and a digital bottom teeth model, comprising:
a top pantograph having a clutch to fit to a top row of teeth, the top pantograph including a first sensor;
a bottom pantograph having a clutch to fit to a bottom row of teeth, the bottom pantograph including a second sensor to communicate with the first sensor to record a physical distance of the first sensor with respect to the second sensor during a first time period; and
a digital bite replicator to, during a second time period, adjust a modeled location of the top teeth model to a modeled location of the bottom teeth model to replicate the physical distance of a digital model of the first sensor with respect to a digital model of the second sensor.

15. The system of claim 14, comprising a computer to record the physical distance of the first sensor with respect to the second sensor during the first time period.

16. The system of claim 15, wherein the computer includes data representative of a shape of the bottom teeth and the top teeth, and is configured to display the orientation of the bottom teeth with respect to the top teeth in association with the physical distance of the first sensor with respect to the second sensor during the first time period.

17. The system of claim 16, wherein the computer includes software configured to detect a bite anomaly.

18. A system for analyzing the bite of a patient, comprising:
a top pantograph having a clutch to fit to a top row of teeth, the top pantograph including a top bow and a first sensor;
a bottom pantograph having a clutch to fit to a bottom row of teeth, the bottom pantograph including a bottom bow and a second sensor, wherein the first sensor and the second sensor communicate to measure a physical distance of the first sensor with respect to the second sensor during a first time period, the first sensor and the second sensor configured to provide a measured distance signal including the measured distance; and a computer to store the measured distance signal, the computer configured to display data representing the top teeth and the bottom teeth during a second time period other than the first, the computer configured to adjust the location of the top teeth with respect to the bottom teeth to replicate the physical distance of the first sensor with respect to the second sensor during the second time period.

19. The system of claim 18, wherein the computer includes software configured to detect a bite anomaly.

20. The system of claim 18, comprising an automatic Stewart platform couplable to the top pantograph and the bottom pantograph to, during a second time period, adjust the location of a first cast of the top row of teeth to a second casting of the bottom row of teeth to replicate the physical distance of the first sensor with respect to the second sensor during a second time period other than the first.

\* \* \* \* \*